United States Patent [19]

Gray et al.

[11] Patent Number: 5,334,327
[45] Date of Patent: Aug. 2, 1994

[54] LATERALLY FLUORINATED 4-CYANOPHENYL AND 4'-CYANOBIPHENYL BENZOATES

[75] Inventors: George W. Gray, Cottingham; David Lacey, Hull; Kenneth J. Toyne, Hull; Michael Hird, Hull; Damien G. McDonnell, Great Malvern, all of England

[73] Assignee: The Secretary of State for Defence in Her Britannic Majesty's Government of the United Kingdom of Great Britain and North Ireland, London, England

[21] Appl. No.: 881,670

[22] Filed: May 12, 1992

Related U.S. Application Data

[62] Division of Ser. No. 571,590, Aug. 30, 1990, Pat. No. 5,156,763.

[30] Foreign Application Priority Data

Feb. 24, 1988 [GB] United Kingdom ............... 8804330

[51] Int. Cl.⁵ .................... C09K 19/20; C09K 19/12; C07C 69/76; G02F 1/13

[52] U.S. Cl. .................... 252/299.67; 252/299.65; 252/299.66; 560/73; 560/102

[58] Field of Search ............ 252/299.67, 299.66, 252/299.65; 560/65, 73, 102

[56] References Cited

U.S. PATENT DOCUMENTS

| | | | |
|---|---|---|---|
| 4,029,594 | 6/1977 | Gavrilovic et al. | 252/299.65 X |
| 4,455,261 | 6/1984 | Sasaki et al. | 558/416 X |
| 4,551,264 | 11/1985 | Eidenschink | 252/299.62 |
| 4,551,280 | 11/1985 | Sasaki et al. | 558/416 X |
| 4,576,733 | 3/1986 | Sugimori et al. | 252/299.67 |
| 4,689,176 | 8/1987 | Inoue et al. | 252/299.65 |
| 4,709,030 | 11/1987 | Petrzilka | 544/242 |
| 4,925,590 | 5/1990 | Reiffenrath et al. | 252/299.61 |
| 4,952,337 | 8/1990 | Bradshaw et al. | 252/299.63 |

Primary Examiner—Richard D. Lovering
Assistant Examiner—C. Harris
Attorney, Agent, or Firm—Nixon & Vanderhye

[57] ABSTRACT

Novel compounds of formula (I), in which R is $R^1$, $R^1O$ or $R^1COO$, where $R^1$ is $C_{1-12}$ alkyl, n and m are 0 or 1 provided that (n+m) is 0 or 1, each of a, b, c and d are independently 0 or 1, provided (a+b+c+d) is not zero, but excluding the case where a and b are 0 and m is 0 and one of c or d is 0 are described, being useful constituents of nematic liquid crystal materials.

10 Claims, 7 Drawing Sheets

Scheme A

Scheme A

Scheme D

Scheme B

Scheme C

Scheme E x = alkyl or alkoxy

Scheme F

LATERALLY FLUORINATED 4-CYANOPHENYL AND 4'-CYANOBIPHENYL BENZOATES

This is a division of application Ser. No. 07/571,590, filed Aug. 30, 1990, U.S. Pat. No. 5,156,763.

This invention relates to laterally fluorinated 4-cyanophenyl and 4'-cyanobiphenyl benzoates, and to liquid crystal mixtures and devices using them.

Liquid crystal materials are well known for use in electro-optical display devices such as calculators, watches and the like. A commonly used type of liquid crystal material is that which shows a nematic liquid crystalline phase. Desirable characteristics in a nematic liquid crystal material include a high nematic to isotropic (N-I) transition temperature, a low solid crystal to nematic (K-I) transition temperature, and the absence of smectic (S) phases. Other desirable characteristics include low viscosity, ease of manufacture, chemical and thermal stability.

Nematic liquid crystal materials generally consist of a mixture of chemical compounds. One class of such compounds are 4-cyano-phenyl and 4' cyanobiphenyl esters of structure:

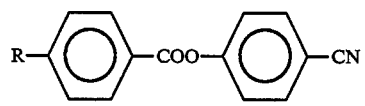

and

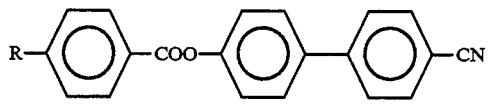

where R may be alkyl, alkoxy, acyloxy or alkylcarbonato disclosed respectively in U.S. Pat. Nos. 4,138,359 and 3,951,846. Some halogenated analogues of these compounds have been investigated, for example fluorinated compounds such as:

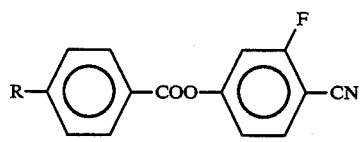

are described in Mol Cryst Liq Cryst 109(2-4), (1984), p169-78 and in Japanese Patent Applications 58/210982, 60/69190, 63/122669, 61/30565 and 61/50953, and German Offenlegungschrift 3339216.

JPA 61/106550 describes compounds of structure:

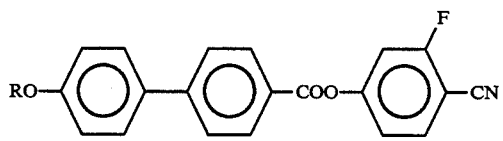

JPA 61/63645 describes the compound:

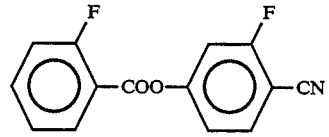

U.S. Pat. No. 4,689,176 discloses optically active compounds of formula:

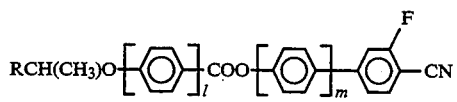

where R is alkyl, l is 1 or 2 and m is 0 or 1.

To date, the extent to which fluorinated compounds for use as liquid crystal compounds could be investigated has been hampered by the unavailability of suitable starting materials, and the difficulties of organofluorine chemistry.

The present inventors have investigated the field of fluorinated 4-cyanophenyl and 4'-cyanobiphenyl esters and have identified a range of novel compounds which are useful components of liquid crystal materials. In the course of this a number of novel and potentially useful fluorinated intermediates have also been prepared.

According to the present invention, novel compounds are provided, having a formula I:

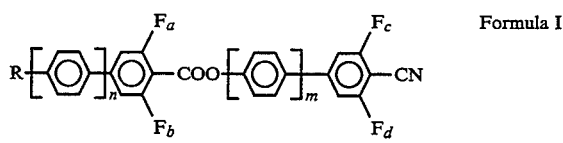

Formula I in which R is $R^1$ or $R^1O$, wherein $R^1$ is $C_1$-$C_{12}$ alkyl, n and m are 0 or 1 provided that (n+m) is 0 or 1, each of a, b, c and d are independently 0 or 1, provided (a+b+c+d) is not zero, but excluding the case where a and b are 0 and one of c or d is one.

Compounds of formula I are useful as constituents of liquid crystal compositions, particularly nematic liquid crystal materials. The structural preferences expressed below are based inter alia on relative usefulness in nematic liquid crystal materials.

Preferably $R^1$ contains 3 to 8 carbon atoms, especially 3, 4 or 5, and $R^1$ is n-alkyl or an asymmetrically substituted alkyl group such as 2-methylbutyl which may be in an optically active or racemic form. It is particularly preferred that R is n-alkyl or n-alkoxy.

Some preferred overall structures for compounds of Formula I are listed in table 1 below.

TABLE 1

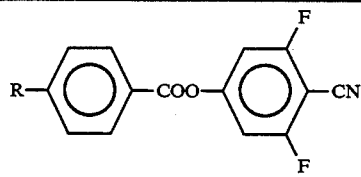

1.1

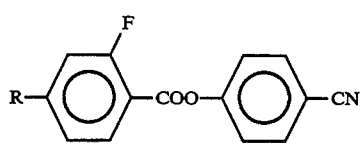

1.2

TABLE 1-continued

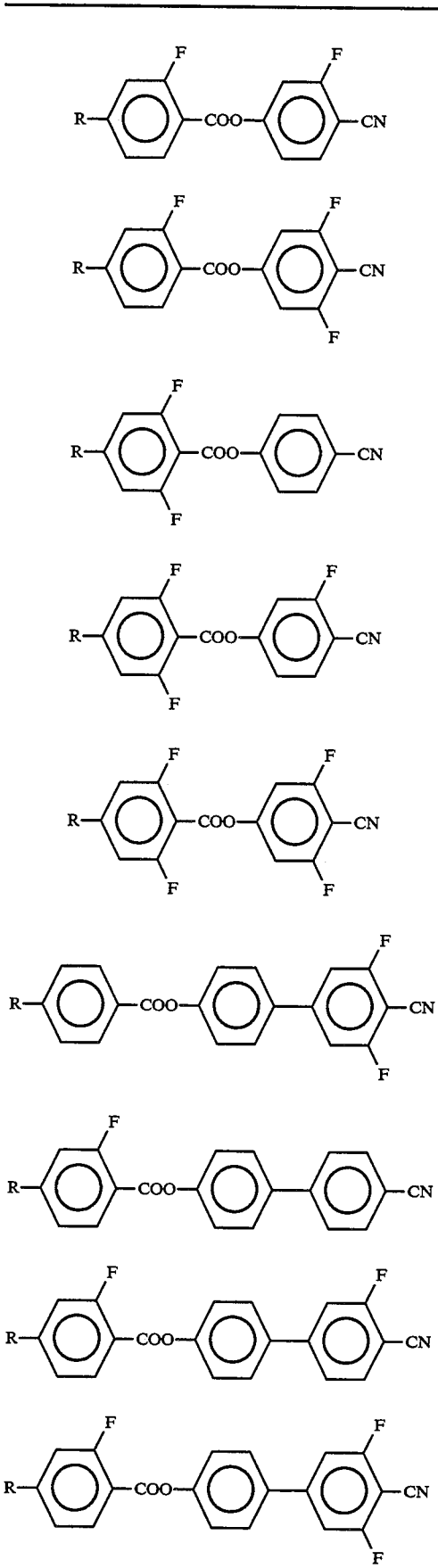

TABLE 1-continued

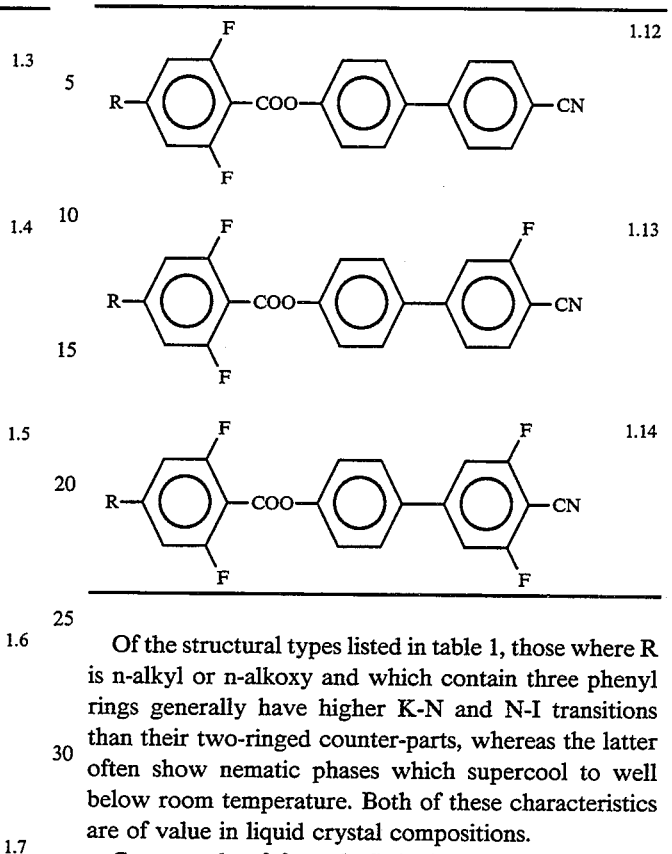

Of the structural types listed in table 1, those where R is n-alkyl or n-alkoxy and which contain three phenyl rings generally have higher K-N and N-I transitions than their two-ringed counter-parts, whereas the latter often show nematic phases which supercool to well below room temperature. Both of these characteristics are of value in liquid crystal compositions.

Compounds of formula I, including those listed in table 1 may be prepared by a number of routes. Being phenylbenzoate esters they may for example be prepared from a phenol and benzoic acid carrying fluorine and other substituents R and CN in appropriate positions. Esterification may be via the dicyclohexylcarbodiimide (DCC) mediated method, the reaction and purification conditions of which are well known to those skilled in the art.

Some fluoro-substituted phenols and benzoic acids are commercially available, such as 3-fluoro-4-cyanophenol, but others may be prepared by synthetic routes.

Suitable fluoro-substituted phenols may be prepared by schemes A and D shown in FIGS. 1 and 2, and suitable fluoro-substituted benzoic acids may be prepared by schemes B and C shown in FIGS. 3 and 4. The steps of these routes are summarised below:

Scheme A

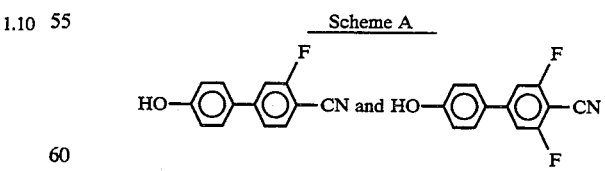

1A (i) Mg, THF; (ii) ($^i$PrO)$_3$B, THF; (iii) 10% HCl.
2A NBS, CH$_2$Cl$_2$.
3A Br$_2$, HOAc.
4A (i) NaNO$_2$, H$_2$SO$_4$; (ii) CuSO$_4$.5H$_2$O, KCN, H$_2$O.
5A Pd(PPh$_3$)$_4$, benzene, 2M—Na$_2$CO$_3$.
6a BBr$_3$, CH$_2$Cl$_2$.

Scheme D

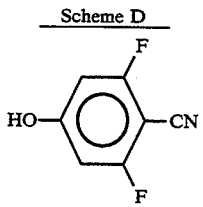

1D (i) nBuLi, THF; (ii) CO$_{2(s)}$, Et$_2$O.
2D Oxalyl chloride, DMF, benzene.
3D 35% ammonia.
4D Thionyl chloride, DMF.
5D AlCl$_3$, NaCl.

Scheme B

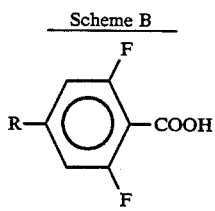

1B (i) Mg, THF; (ii) CH$_3$(CH$_2$)$_3$CHO, Et$_2$O.
2B P$_2$O$_5$, pentane.
3B 5% Pd/C, pentane, H$_2$.
4B (i) nBuLi, THF; (ii) CO$_{2(s)}$, Et$_2$O.
5B (i) nBuLi, THF; (ii) ($^i$PrO)$_3$B, THF; (iii) 10% HCl.
6B C$_4$H$_9$Br, K$_2$CO$_3$, acetone

Scheme C

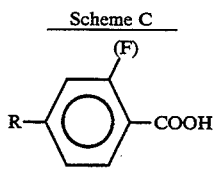

1C (i) Pent-1-yne, nBuLi, THF; (ii) ZnCl$_2$, THF; (iii) compound 3, Pd(PPh$_3$)$_4$, THF.
2C 5% Pd/C, EtOH, H$_2$.
3C Conc. H$_2$SO$_4$, water, HOAc.
4C C$_4$H$_9$Br, K$_2$CO$_3$, acetone.
5C (i) C$_4$H$_9$Br, EtOH, water, NaOH; (ii) 36% HCl.

Known acids which may be used in the esterification reaction include non-fluorinated 4-alkyl and 4-alkoxy benzoic acids, and 4-alkyl and 4-alkoxy phenyl-4'-benzoic acids. These may be used to prepare structures 1.1 and 1.8 listed in table 1 above and other compounds of formula I in which a and b are both O, and n is 0 or 1.

Compounds of formula I are suitable components of liquid crystal materials, particularly nematic liquid crystal materials.

According to a further aspect of the invention there is therefore provided a liquid crystal material, being a mixture of at least two compounds, at least one of which is a compound of formula I.

The material may contain two or more compounds of formula I, for example differing only in their substituent R, eg two different n-alkyl and/or n-alkoxy groups. Preferably the materials according to this aspect of the invention contains one or more compounds having a high dielectric anisotropy, and selected from table 2 below:

TABLE 2

| | |
|---|---|
| 2.1 | R$^2$—⬡—⬡—CN |
| 2.2 | R$^2$—◯—◯—CN |
| 2.3 | R$^2$—◯—CH$_2$CH$_2$—⬡—CN |
| 2.4 | R$^2$—(N,N pyrimidine)—⬡—CN |
| 2.5 | R$^2$—◯—◯—CN |
| 2.6 | R$^2$—◯—COO—⬡—CN |
| 2.7 | R$^2$—⬡—COO—⬡—CN |
| 2.8 | R$^2$—⬡—⬡—⬡—CN | where R$^2$ is alkyl or alkoxy containing 3 to 10 carbon atoms. It is especially preferred that the material contains one or more compounds of formula 2.1, optionally together with one or more compounds of formula 2.8.

The liquid crystal material of this aspect of the invention may also contain compounds of low dielectric anisotropy, for example one or more compounds as listed below in table 3:

TABLE 3

| | |
|---|---|
| 3.1 | R$^3$—⬡—COO—⬡(X)—R$^4$ |
| 3.2 | R$^3$—⬡—COO—⬡(X)—R$^4$ |
| 3.3 | R$^3$—⬡—COO—⬡—R$^4$ |

TABLE 3-continued

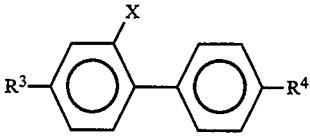 3.4

 3.5

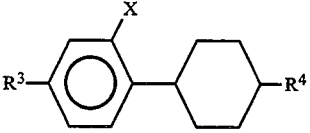 3.6

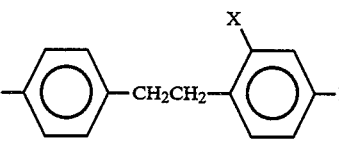 3.7

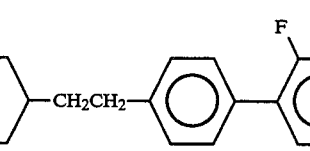 3.8

Where $R^3$ and $R^4$ are independently $C_3$ to $C_{10}$ alkyl or alkoxy and X is fluorine or hydrogen.

Typically but not exclusively a liquid crystal material of this aspect of the invention will contain:

| | |
|---|---|
| high dielectric anisotropy compound(s) eg as listed in table 2 | 50–95 wt % |
| low dielectric anisotropy compound(s) eg as listed in table 3 | 0–50 wt % |
| compound(s) of formula I | 5–50 wt % |
| additives | 0–10 wt % | the total being 100 wt %.

Additives may for example include pleochroic dyes, e.g. one or more of those described in EP-A-82300891.

The liquid crystal material of this aspect of the invention may be used in any of the known types of nematic liquid crystal device, for example: the twisted nematic effect device, which may be multiplexed; the Freedericksz effect device using materials of positive or negative dielectric anisotropy; the cholesteric memory mode device; the cholesteric to nematic phase change effect device (these latter two devices require a material which contains one or more optically active compounds, for example a compound of formula I, or a compound as listed in table 2 or 3 in which R, $R^2$, $R^3$ or $R^4$ is a group containing an asymmetrically substituted carbon atom, in particular (+) or (−) 2-methylbutyl or 2-methylbutyloxy), the dynamic scattering effect device or the two frequency switching effect device. A liquid crystal electro-optic display device which uses a liquid crystal material that is a mixture of at least two compounds, one of which is a compound of formula I is a further aspect of this invention. The method of construction and operation of such devices is well known in the art.

BRIEF DESCRIPTION OF DRAWINGS

The invention will now be described by way of example only with reference to.

EXAMPLE 1

Scheme A

4-Methoxyphenylboronic acid (1). (Step 1A)

Figure 1:
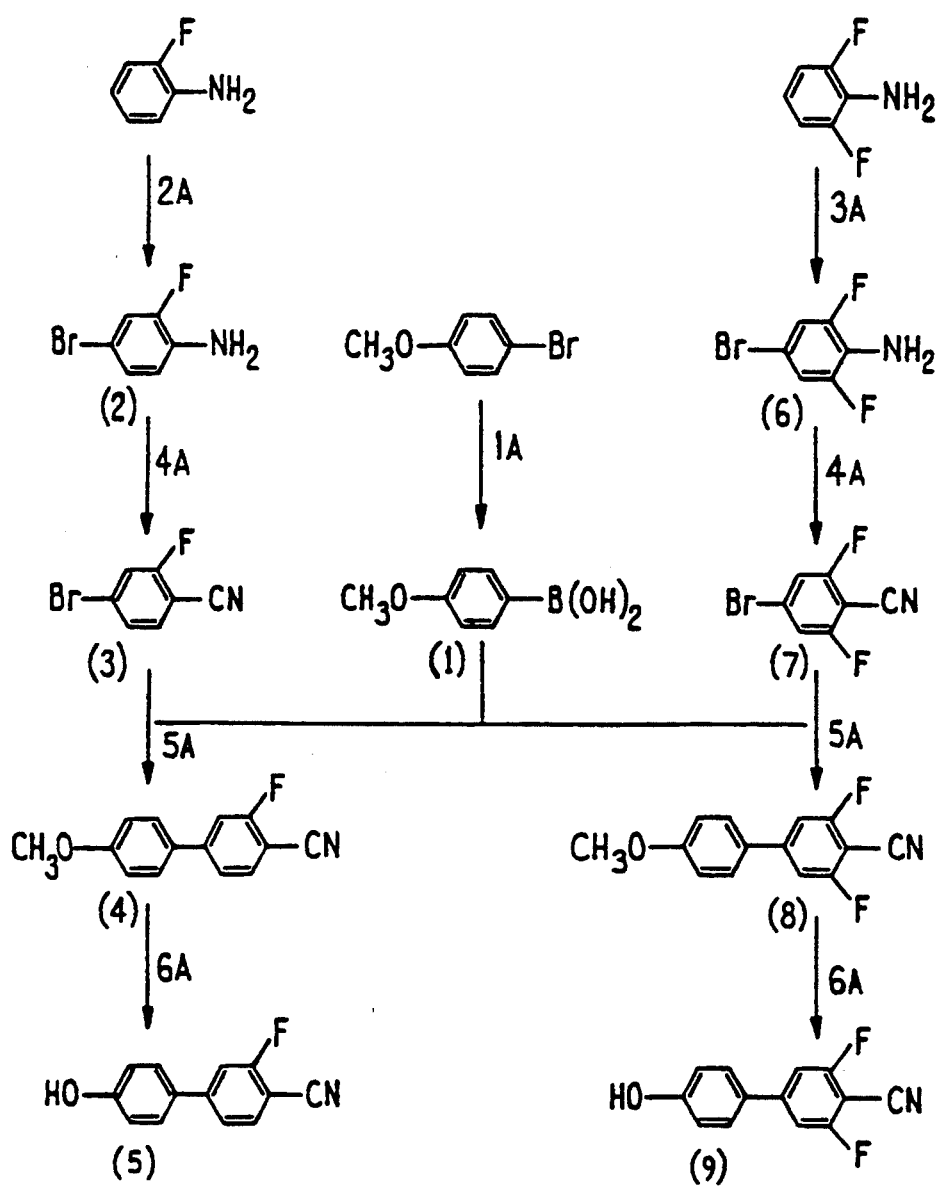
FIGS. 1, 2, 3 and 4 showing preparative routes to fluorinated phenols and benzoic acids.
Figure 2:
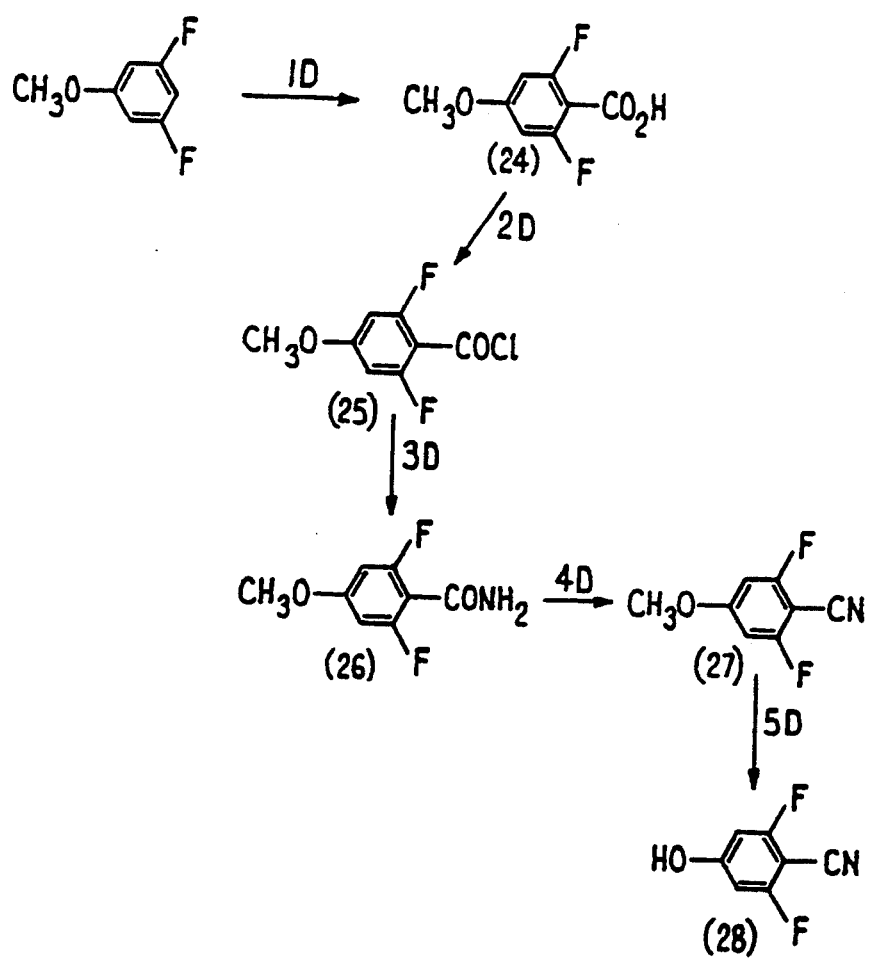
Figure 3:
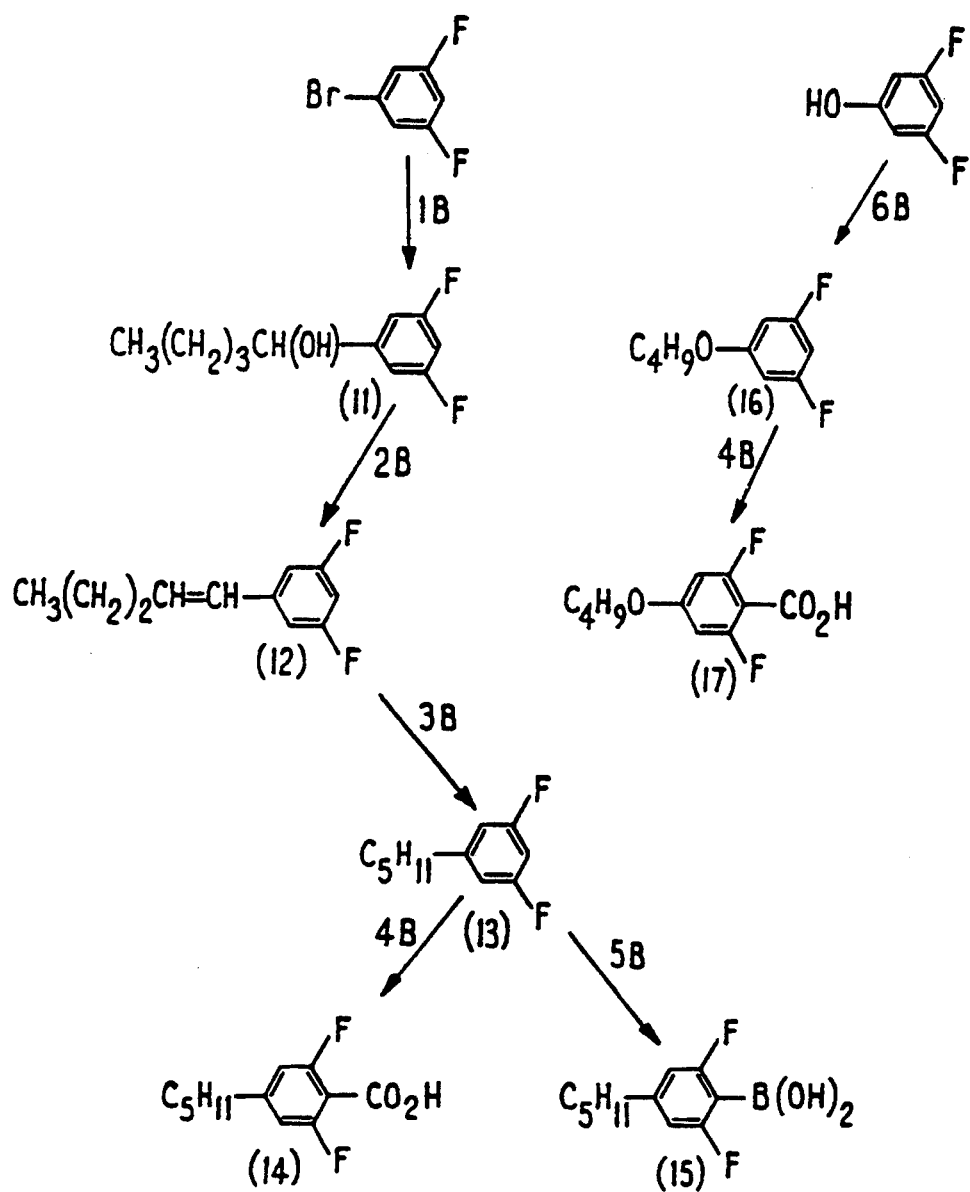
Figure 4:
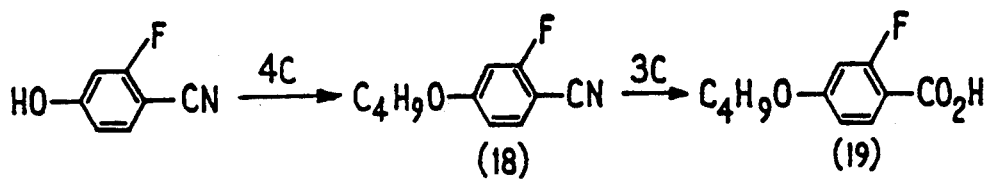
Figure 4:
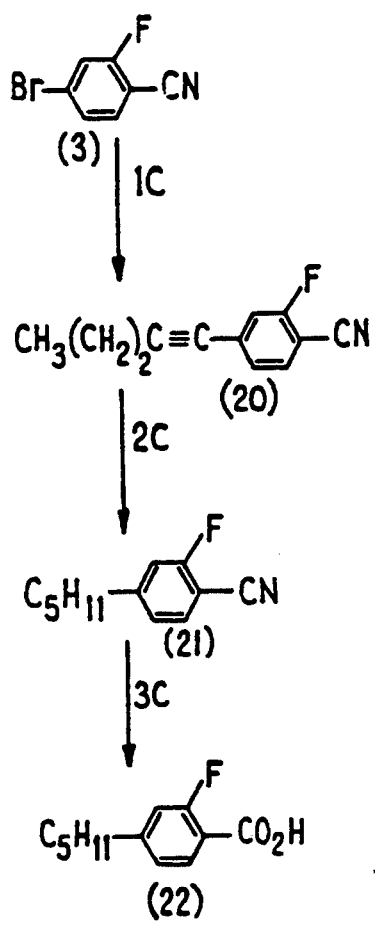
Figure 4:
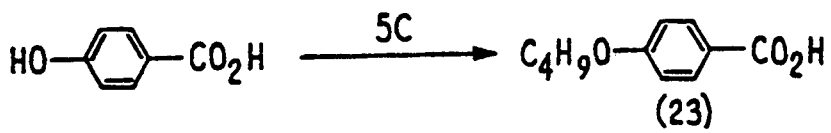

A solution of the Grignard reagent, prepared from 4-bromoanisole (80.0 g, 0.43 mol) and magnesium (11.96 g, 0.49 mol) in dry THF (300 ml) was added dropwise to a stirred, cooled (−78° C.) solution of tri-isopropyl borate (161.7 g, 0.86 mol) in dry THF (50 ml) under dry nitrogen. The stirred mixture was allowed to warm to room temperature overnight and was then stirred at room temperature for 1 h with 10% hydrochloric acid (300 ml). The product was extracted into ether (twice), the combined ethereal extracts were washed with water and dried (MgSO₄). The solvent was removed in vacuo to yield a cream-coloured solid (58.5 g) which was recrystallised from water to give colourless crystals.

Yield 27.7 g, 43%.

mp 201°–202° C.

Note: A cream-coloured oil was separated during the above recrystallisation which solidified on cooling to give a cream-coloured solid.

Yield 17.5 g.

4-Bromo-2-fluoroaniline (2). (Step 2A)

N-Bromosuccinimide (160.4 g, 0.90 mol) was added in small portions to a stirred, cooled solution of 2-fluoroaniline (100.0 g, 0.90 mol) in dry dichloromethane (400 ml). The stirred mixture was allowed to warm to 0° C. over 45 min, washed with water and dried (MgSO₄). The solvent was removed in vacuo to yield a red solid (180 g) which was steam distilled to give a colourless solid.

Yield 120.0 g, 70%.

mp 41°–42° C.

4-Bromo-2-fluorobenzonitrile (3). (Step 4A)

Concentrated sulphuric acid (60 ml) was added dropwise to a stirred mixture of compound 2 (75.0 g, 0.39 mol), water (150 ml) and glacial acetic acid (185 ml). The clear solution was cooled to −5° C. (an emulsion formed) and a solution of sodium nitrite (30.0 g, 0.44 mol) in water (100 ml) was added dropwise; the stirred mixture was maintained at −5° C. for 15 min.

A solution of potassium cyanide (128.3 g, 1.98 mol) in water (300 ml) was added dropwise to a stirred solution of copper (II) sulphate pentahydrate (118.1 g, 0.48 mol) in water (300 ml) and ice (300 g) at 10°–20° C. Sodium hydrogen carbonate (265.1 g, 3.16 mol) and cyclohexane (450 ml) were added, the temperature was raised to 50° C. and the cold diazonium salt mixture was added in portions with rapid stirring. The mixture was cooled, the organic layer was separated and the aqueous layer was washed with ether (twice). The combined organic phases were washed with water, 10% sodium hydroxide, water and dried (MgSO₄). The solvent was removed in vacuo to afford a dark brown solid (78.0 g) which was steam distilled to give an off-white solid.
Yield 59.2 g, 76%.
mp 69°–70° C.

4-Cyano-3-fluoro-4'-methoxybiphenyl (4). (Step 5A)

A solution of compound 1 (10.64 g, 0.07 mol) in ethanol (90 ml) was added dropwise to a stirred mixture of compound 3 (12.0 g, 0.06 mol) and tetrakis (triphenylphosphine) palladium (0) (2.10 g, 1.82 mmol) in benzene (125 ml) and 2M-sodium carbonate (100 ml) at room temperature under dry nitrogen. The stirred mixture was heated under reflux (90°–95° C.) for 2.5 h (i.e., until glc analysis revealed absence of starting material). The mixture was cooled and stirred for 1 h at room temperature with 30% hydrogen peroxide (2 ml). The mixture was cooled further to 2° C., the product was filtered off and washed with water. The product was dried (CaCl$_2$) in vacuo to give a yellow powder.
Yield 11.9 g, 88%.
mp 153°–154° C.

4-Cyano-3-fluoro-4'-hydroxybiphenyl (5). (Step 6A)

A solution of boron tribromide (12.0 ml, 31.8 g, 0.13 mol) in dry dichloromethane (100 ml) was added dropwise to a stirred, cooled (−78° C.) solution of compound 4 (14.0 g, 0.06 mol) in dry dichloromethane (250 ml) under dry nitrogen. The stirred mixture was allowed to warm. to room temperature over 20 h (i.e., until glc analysis revealed absence of starting material). Water was added and a yellow precipitate was produced. The product was extracted into ether (twice), and the combined ethereal extracts were washed with water and dried (MgSO$_4$). The solvent was removed in vacuo to afford a pale-yellow powder.
Yield 13.1 g, 100%.
mp 201°–202° C.

4-Bromo-2,6-difluoroaniline (6). (Step 3A)

A solution of bromine (127.0 g, 0.79 mol) in glacial acetic acid (200 ml) was added slowly, dropwise to a stirred solution of 2,6-difluoroaniline (101.5 g, 0.79 mol) in glacial acetic acid (550 ml) keeping the temperature below 25° C. The mixture was stirred at room temperature for 2 h, and then sodium thiosulphate (50 g), sodium acetate (125 g) and water (700 ml) were added and the mixture was cooled in a refrigerator overnight. The product was filtered off, dissolved in ether, and the ether phase was washed with water, 10% sodium hydroxide, water and dried (MgSO$_4$). The solvent was removed in vacuo to yield a pale yellow solid (134 g) which was steam distilled to give a colourless solid.
Yield 117.9 g, 72%.
mp 67°–68° C.

4-Bromo-2,6-difluorobenzonitrile (7). (Step 4A)

A stirred mixture of compound 6 (56.0 g, 0.27 mol) and concentrated sulphuric acid-water (1:1, 250 ml) was heated until a solution was obtained. The mixture was cooled to −10° C. and a solution of sodium nitrite (30.9 g, 0.45 mol) in water (70 ml) was added dropwise. The mixture was stirred at −5° C. for 2.5 h.

A solution of potassium cyanide (97.5 g, 1.50 mol) in water was added dropwise to a stirred solution of copper(II) sulphate pentahydrate (86.5 g, 0.35 mol) in water (200 ml) and ice (130 g). Sodium hydrogen carbonate (300 g), cyclohexane (1200 ml) and glacial acetic acid (130 ml) were added, the temperature was raised to 50° C. and the cold diazonium salt mixture was added in portions with rapid stirring. The mixture was cooled, the organic layer was separated and the aqueous layer was washed with ether (twice). The combined organic phases were washed with water, 10% sodium hydroxide, water and dried (MgSO$_4$). The solvent was removed in vacuo to afford a dark-brown solid (58.5 g) which was steam distilled to give a light-orange solid.
Yield 31.7 g, 54%.
mp 79°–80° C.

4-Cyano-3,5-difluoro-4'-methoxybiphenyl (8). (Step 5A)

A solution of compound 1 (11.50 g, 0.076 mol) in ethanol (90 ml) was added dropwise to a stirred mixture of compound 7 (15.0 g, 0.069 mol) and tetrakis(triphenylphosphine)palladium(0) (2.38 g, 2.06 mmol) in benzene (130 ml) and 2M-sodium carbonate (100 ml) at room temperature under dry nitrogen. The stirred mixture was heated under reflux (90°–95° C.) for 4.5 h (i.e., until glc analysis revealed absence of starting material). The mixture was cooled and stirred for 1 h at room temperature with 30% hydrogen peroxide (2 ml). The mixture was further cooled to 2° C., and the product was filtered off and washed with water. The product was dried (CaCl$_2$) in vacuo to give fawn-coloured needles.
Yield 14.1 g, 84%.
mp 205°–207° C.

4-Cyano-3,5-difluoro-4'-hydroxybiphenyl (9). (Step 6A)

A solution of boron tribromide (25.0 ml, 61.5 g, 0.25 mol) in dry dichloromethane (140 ml) was added dropwise to a stirred, cooled (−78° C.) solution of compound 8 (12.22 g, 0.05 mol) in dry dichloromethane (250 ml) under dry nitrogen. The stirred mixture was allowed to warm to room temperature over 9 h (i.e., until glc analysis revealed absence of starting material). The mixture was cooled to −10° C., water was added slowly (exothermic) and cooled to 2° C. The product was filtered off, washed with water and dried (CaCl$_2$) in vacuo to give a pale-yellow powder.
Yield 13.3 g, 100%.
mp 230°–231° C.

EXAMPLE 2

Scheme D 2,6-Difluoro-4-methoxybenzoic acid (24). (Step 1D)

A solution of n-butyllithium (10.0M in hexane; 25.0 ml, 0.25 mol) was added dropwise to a stirred, cooled (−78° C.) solution of 3,5-difluoroanisole (35.9 g, 0.25 mol) in dry THF (200 ml) under dry nitrogen. The stirred mixture was maintained under these conditions for 2.5 h and then poured into a slurry of solid carbon dioxide and dry ether. The product was extracted into 10% sodium hydroxide (twice), the combined basic extracts were acidified with 36% hydrochloric acid, and the product was extracted into ether (twice), the combined ethereal extracts were washed with water and dried (MgSO$_4$). The solvent was removed in vacuo to give a colourless solid.
Yield 46.5 g, 99%.
mp 184°–185° C.

2,6-Difluoro-4-methoxybenzoyl chloride (25). (Step 2D)

A solution of oxalyl chloride (36.5 g, 0.29 mol) in dry benzene (50 ml) was added dropwise to a stirred solution of compound 24 (25.5 g, 0.14 mol) and dry DMF (40 drops) in dry benzene (500 ml) at room temperature. The mixture was stirred at room temperature overnight and the excess of oxalyl chloride and benzene were removed in vacuo.

2,6-Difluoro-4-methoxybenzamide (26). (Step 3D)

The crude acid chloride (25) was dissolved in dry diglyme (60 ml) and added dropwise at room temperature with gentle stirring to 35% ammonia (750 ml). The resulting colourless precipitate was filtered off and dried ($CaCl_2$) in vacuo to give a colourless solid.
Yield 21.2 g, 81%.
mp 158°–159° C.

2,6-Difluoro-4-methoxybenzonitrile (27). (Step 4D)

A solution of thionyl chloride (139.0 g, 1.17 mol) in dry DMF (150 ml) was added to a stirred solution of compound 26 (20.0 g, 0.11 mol) in dry DMF (250 ml) at room temperature. The mixture was stirred at room temperature overnight and then poured onto ice-water. The product was extracted into ether (twice), and the combined ethereal extracts were washed with water, saturated sodium hydrogen carbonate, water and dried ($MgSO_4$). The solvent was removed in vacuo to give off-white crystals.
Yield 17.7 g, 95%.
mp 59°–60° C.

2,6-Difluoro-4-hydroxybenzonitrile (28). (Step 5D)

A stirred, homogeneous mixture of finely powdered, compound 27 (17.0 g, 0.10 mol), aluminium chloride (29.4 g, 0.22 mol) and sodium chloride (7.1 g, 0.12 mol) was heated to 180° C. over 25 min and then at 180° C. for 1 h (glc and tlc analysis both revealed a complete reaction). Ice-water was added, and the product was extracted into ether (twice). The combined ethereal extracts were washed with water, and the product was extracted into 10% sodium hydroxide (twice) and the combined basic extracts were acidified with 36% hydrochloric acid. The product was extracted into ether (twice), and the combined ethereal extracts were washed with water and dried ($MgSO_4$). The solvent was removed in vacuo to give a fawn solid.
Yield 14.6 g, 94%.
mp 119°–120° C.

EXAMPLE 3

Scheme B.

1-(3,5-Difluorophenyl)pentan-1-ol (11). (Step 1B)

A solution of pentanal (19.0 g, 0.22 mol) in dry ether (75 ml) was added dropwise to a stirred solution of the Grignard reagent at room temperature, under dry nitrogen, prepared from 1-bromo-3,5-difluorobenzene (50.2 g, 0.26 mol) and magnesium (7.25 g, 0.30 mol) in dry THF (100 ml). The stirred mixture was heated under reflux for 2 h, cooled and a saturated solution of ammonium chloride (300 ml) was added. The product was extracted into ether (twice), and the combined ethereal extracts were washed with water and dried ($MgSO_4$). The solvent was removed in vacuo to give a pale-orange liquid (51.1 g) which was distilled to yield a colourless liquid. Smaller quantities of crude product were purified by column chromatography (silica gel/dichloromethane) to yield a colourless liquid (92%).
Yield 35.8 g, 69%.
bp 90° C. at 0.5 mm Hg.

3,5-Difluoro-1-pent-1'-enylbenzene (12). (Step 2B)

Phosphorus(V) oxide (64.5 g, 0.45 mol) was added in portions to a stirred solution of compound 11 (35.0 g, 0.175 mol) in dry pentane (150 ml) at room temperature. The mixture was stirred at room temperature overnight (glc analysis revealed absence of starting material) and filtered.

3,5-Difluoro-1-pentylbenzene (13). (Step 3B)

5% Palladium-on-charcoal (4.0 g) was added to the above filtrate [i.e. compound 12 in pentane (150 ml)] at room temperature. The stirred mixture was hydrogenated at atmospheric pressure for 4 h (i.e., until glc analysis revealed absence of starting material) and the mixture was filtered. The majority of the pentane was removed in vacuo, and the final amount of pentane was distilled off (760 mm Hg) at 38° C. and the residue was then distilled to yield a colourless liquid.
Yield 23.4 g, 73%.
bp 200° C. at 760 mm Hg.

2,6-Difluoro-4-pentylbenzoic acid (14). (Step 4B)

A solution of n-butyllithium (10.5M in hexane; 2.70 ml, 0.028 mol) was added dropwise to a stirred, cooled (−78° C.) solution of compound 13 (5.10 g, 0.028 mol) in dry THF (30 ml) under dry nitrogen. The stirred mixture was maintained under these conditions for 2.5 and then poured onto a slurry of solid carbon dioxide and dry ether. The product was extracted into 10% sodium hydroxide which was then acidified with 36% hydrochloric acid. The acidic mixture was washed with ether (twice), and the combined ethereal layers were washed with water and dried ($MgSO_4$). The solvent was removed in vacuo to yield a colourless solid.
Yield 5.8 g, 91%.
mp 75°–76° C.

2,6-Difluoro-4-pentylphenylboronic acid (15). (Step 5B)

A solution of n-butyllithium (10.4M in hexane; 2.70 ml, 0.028 mol) was added dropwise to a stirred, cooled (−78° C.) solution of compound 13 (5.00 g, 0.027 mol) in dry THF (60 ml) under dry nitrogen. The stirred mixture was maintained under these conditions for 2.5 h and a previously cooled solution of tri-isopropyl borate (10.22 g, 0.054 mol) in dry THF (50 ml) was added dropwise at −78° C. The stirred mixture was allowed to warm to room temperature overnight and stirred for 1 h with 10% hydrochloric acid (30 ml). The product was extracted into ether (twice), and the combined ethereal extracts were washed with water and dried ($MgSO_4$). The solvent was removed in vacuo to give a colourless solid.
Yield 6.7 g, 100%.
mp 95°–100° C.

1-Butoxy-3,5-difluorobenzene (16). (Step 6B)

A solution of 1-bromobutane (11.0 g, 0.08 mol) in acetone (30 ml) was added dropwise to a stirred, refluxing mixture of 3,5-difluorophenol (9.1 g, 0.07 mol) and potassium carbonate (30 g, 0.2 mol) in acetone (200 ml). The stirred mixture was heated under reflux for 24 h (glc analysis revealed absence of starting material). The product was extracted into ether (twice), and the combined ethereal extracts were washed with water, 5% sodium hydroxide, water and dried (MgSO$_4$). Most of the solvent was removed in vacuo, and after the removal of the final amount of solvent and the excess of 1-bromobutane at atmospheric pressure, the residue was distilled to yield a colourless liquid.

Yield 11.7 g, 90%.

bp 204° C. at 760 mm Hg.

4-Butoxy-2,6-difluorobenzoic acid (17). (Step 4B)

A solution of n-butyllithium (10.5M in hexane; 3.60 ml, 0.038 mol) was added dropwise to a stirred, cooled (−78° C.) solution of compound 16 (7.00 g, 0.038 mol) in dry THF (35 ml) under dry nitrogen. The stirred mixture was maintained under these conditions for 2.5 h and then poured onto a slurry of solid carbon dioxide and dry ether. The product was extracted into 10% sodium hydroxide which was then acidified with 36% hydrochloric acid. The product was filtered off and dried (CaCl$_2$) in vacuo to give a colourless solid.

Yield 8.3 g, 96%.

mp 110°-112° C.

EXAMPLE 4

Scheme C

4-Butoxy-2-fluorobenzonitrile (18). (Step 4C)

A solution of 1-bromobutane (18.0 g, 0.13 mol) in acetone (30 ml) was added dropwise to a stirred refluxing mixture of 2-fluoro-4-hydroxybenzonitrile (15.0 g, 0.11 mol) and potassium carbonate (46.0 g, 0.33 mol) in acetone (300 ml). The stirred mixture was heated under reflux for 21 h (glc analysis revealed absence of starting material). The product was extracted into ether (twice), and the combined ethereal extracts were washed with water, 5% sodium hydroxide, water and dried (MgSO$_4$). The solvent and the excess of 1-bromobutane were removed in vacuo to yield a pale-orange solid.

Yield 19.5 g, 93%.

mp 25°-26° C.

4-Butoxy-2-fluorobenzoic acid (19). (Step 3C)

A mixture of concentrated sulphuric acid (190 ml) and water (190 ml) was added dropwise to a stirred solution of compound 18 (19.0 g, 0.098 mol) in glacial acetic acid (380 ml). The stirred mixture was heated under reflux for 48 h, cooled in a refrigerator for 24 h and the product was filtered off and dried (CaCl$_2$) in vacuo to give pale-yellow crystals.

Yield 18.7 g, 90%.

mp 93°-95° C.

2-Fluoro-4-pent-1′-yn-1′-ylbenzonitrile (20). (Step 1C)

A solution of n-butyllitium (10.0M in hexane; 10.0 ml, 0.10 mol) was added dropwise to a stirred, cooled (<0° C.) solution of pent-1-yne (6.80 g, 0.10 mol) in dry THF* (51 ml) under dry nitrogen. This mixture was stirred for 10 min and then a solution of zinc chloride* (13.63 g, 0.10 mol) in dry THF* (100 ml) was added dropwise at <0° C. The mixture was stirred at room temperature for 15 min and a solution of compound 3 (20.0 g, 0.10 mol) in dry THF* (100 ml) followed by a solution of tetrakis(triphenylphosphine)palladium(0) (2.31 g, 2.0 mmol) in dry THF* (25 ml) were added dropwise at <0° C. The mixture was stirred at room temperature for 20 h (glc analysis revealed absence of starting material; 20 h was probably longer than required for reaction) and poured into 10% hydrochloric acid (200 ml). The product was extracted into ether (twice), and the combined ethereal extracts were washed with water, saturated sodium hydrogen carbonate, water and dried (MgSO$_4$). The solvent was removed in vacuo to afford an orange liquid which was distilled to yield a pale-yellow oil.

Yield 17.6 g, 94%.

bp 100°-105° C. at 0.1 mm Hg.

Note.

* Sodium dried THF was distilled from lithium aluminium hydride and kept over a molecular sieve (type 4A).

Zinc chloride (ACS reagent) was dried overnight at 100° C.

2-Fluoro-4-pentylbenzonitrile (21). (Step 2C)

A stirred mixture of compound 20 (16.0 g, 0.085 mol) and 5% palladium-on-charcoal (4.00 g) in ethanol (100 ml) was hydrogenated at atmospheric pressure for 8 h (glc analysis revealed absence of starting material). The catalyst was filtered off and the solvent was removed in vacuo to yield a pale-orange semi-solid.

Yield 15.35 g, 95%.

mp not recorded, probably around 20° C.

2-Fluoro-4-pentylbenzoic acid (22). (Step 3C)

A mixture of concentrated sulphuric acid (150 ml) and water (150 ml) was added dropwise to a stirred solution of compound 21 (15.0 g, 0.078 mol) in glacial acetic acid (300 ml). The stirred mixture was heated under reflux for 48 h, cooled in a refrigerator overnight and the product was filtered off. The product was dissolved in ether, extracted into 10% sodium hydroxide, which was then acidified with 36% hydrochloric acid, washed with ether (twice), and the combined ethereal phases were washed with water and dried (MgSO$_4$). The solvent was removed in vacuo to give a brown crystalline solid.

Yield 11.5 g, 70%.

mp 90°-91° C.

4-Butoxybenzoic acid (23). (Step 5C)

1-Bromobutane (22.6 g, 0.165 mol) was added dropwise at room temperature to a stirred mixture of 4-hydroxybenzoic acid (15.0 g, 0.11 mol) in ethanol (60 ml) and sodium hydroxide (10.60 g) in the minimum amount of water. The stirred mixture was heated under reflux overnight (tlc analysis revealed a complete reaction), and then the ethanol was distilled off and an equal volume of water was added. The mixture was boiled to give a solution, cooled, washed with ether and acidified with 36% hydrochloric acid. The cooled mixture was filtered, and the product was washed with water to give a colourless solid (13.9 g) which was recrystallised from ethanol to give colourless crystals.

Yield 12.1 g, 57%.

mp 149°-150° C.

Although illustrated in examples 1, 2, 3 and 4 above, and in FIGS. 1, 2, 3 and 4 for the preparation of the n-pentyl and n-butyloxy substituted acids, schemes B and C were found to be equally suitable for the preparation of all corresponding $C_1$-$C_{12}$ alkyl and alkoxy substituted compounds.

EXAMPLE 5

Using schemes E and F shown in FIGS. 5 and 6, the steps of which are listed below, the compounds of formula I listed in tables 4 and 5 were prepared.

Scheme E (i) HO—⟨⟩—CN (ii) HO—⟨⟩—CN (with F)

(iii) HO—⟨⟩—CN (with 2 F)

(iv) dicyclohexylcarbodiimide, 4-(N-pyrrolidino)pyridine, CH₂Cl₂

Scheme F (i) HO—⟨⟩—⟨⟩—CN

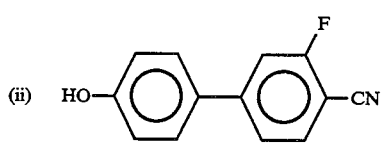

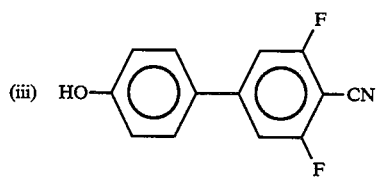

Figure 5:
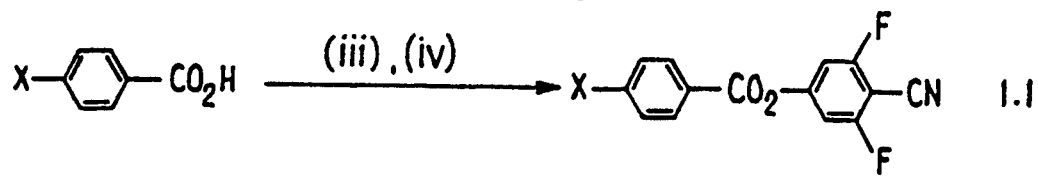
FIGS. 5 and 6 showing routes to compounds of formula I.
Figure 5:
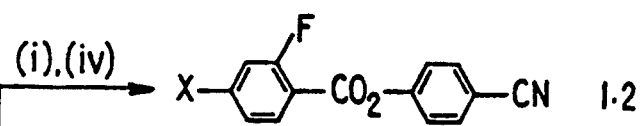
Figure 5:
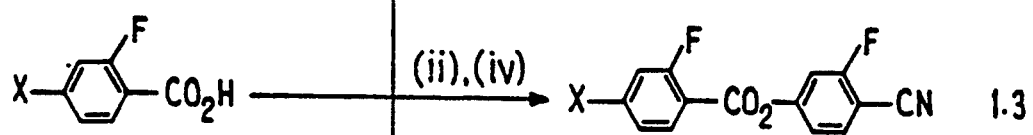
Figure 5:
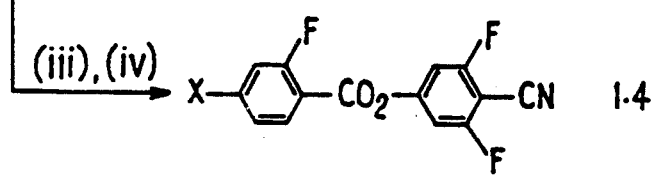
Figure 5:
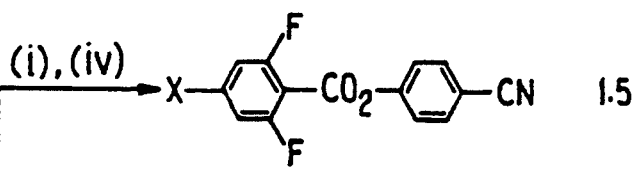
Figure 5:
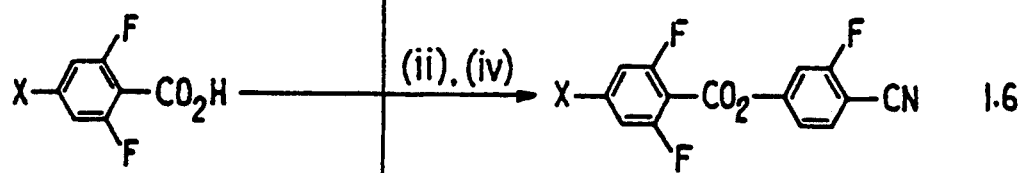
Figure 5:
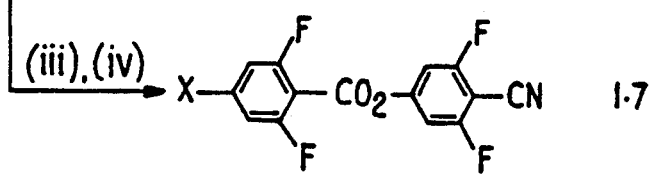
Figure 6:
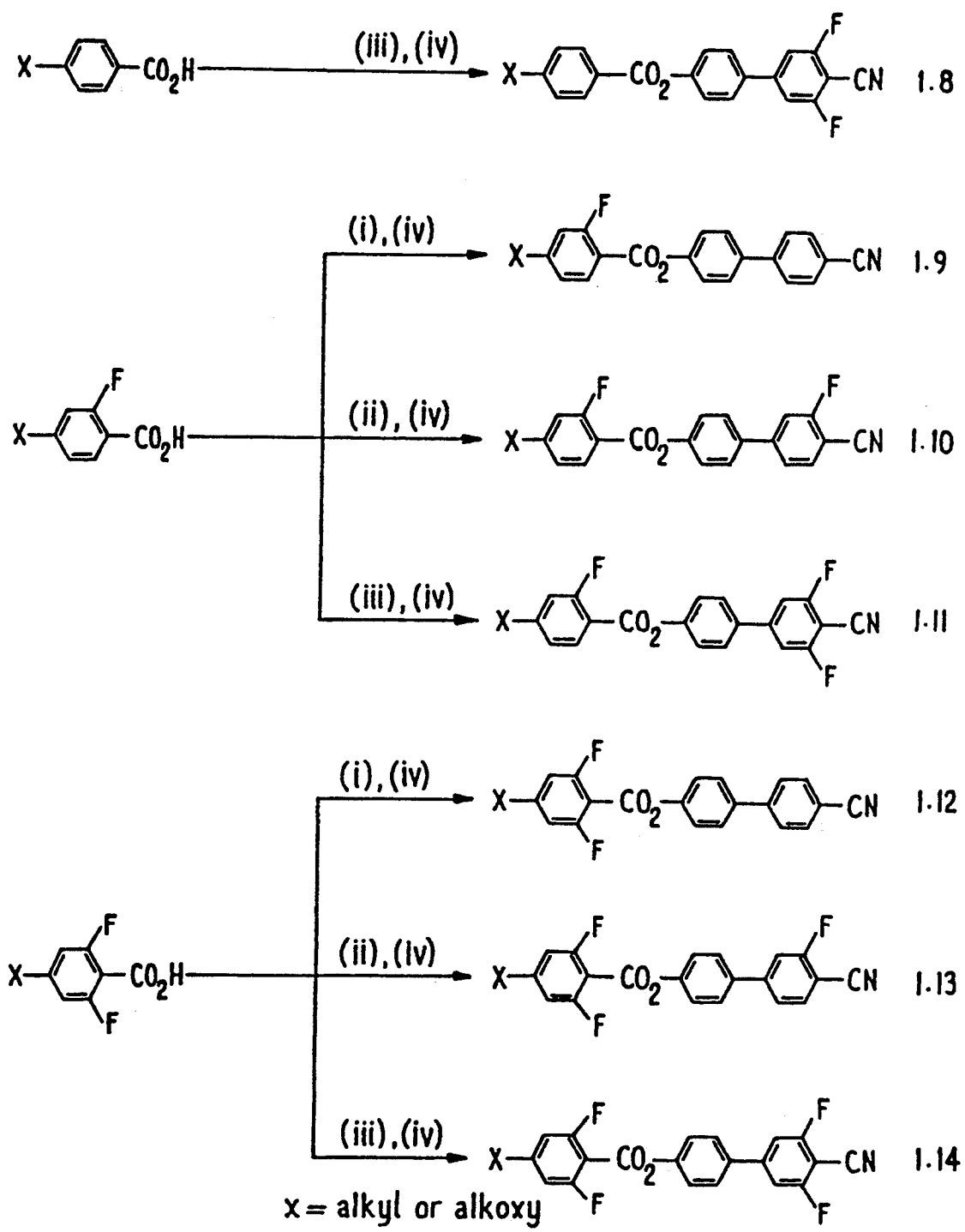

In FIGS. 5 and 6, X is alkyl or alkoxy.

The experimental method was as follows:

A solution of dicyclohexylcarbodiimide (DCC) (1.15 mol equivalent) in dry dichloromethane (50 ml) was added dropwise to a stirred solution of the appropriate carboxylic acid (1 mol equivalent), the appropriate phenol (1 mol equivalent) and 4-(N-pyrrolidino)pyridine (0.30 mol equivalent) in dry dichloromethane (55 ml) at room temperature. The mixture was stirred at room temperature overnight and the N,N'-dicyclohexylurea (DCU) was filtered off. The filtrate was washed successively with water, 5% acetic acid, water and dried (MgSO$_4$). The solvent was removed in vacuo and the residue was purified by column chromatography (silica gel/dichloromethane) to give a solid which was recrystallised from ethanol (with charcoal decolourisation where required) to yield colourless crystals.

A number of compounds of formula I were prepared, and are listed, together with their liquid crystal properties, in tables 4 and 5 below. The preparative routes which were employed to make the phenol and benzoic acid which were esterified using the DCC mediated method are also indicated in tables 4 and 5. 'Known' in table 4 and 5 indicates that commercially available or known acids or phenols were used.

TABLE 4

| Structure | R | Acid Route | Phenol Route | K-N(°C.) | K-I(°C.) | N-I(°C.) |
|---|---|---|---|---|---|---|
| 1.1 | C$_5$H$_{11}$ | C | D | — | 29.5 | (−8.0) |
| 1.1 | C$_4$H$_9$O | C | D | — | 71.5 | (7.5) |
| 1.2 | C$_5$H$_{11}$ | C | Known | — | 65.5 | (32.0) |
| 1.2 | C$_4$H$_9$O | C | Known | — | 90.0 | (61.0) |
| 1.3 | C$_5$H$_{11}$ | C | Known | — | 39.5 | (−3.0) |
| 1.3 | C$_4$H$_9$O | C | Known | — | 55.0 | (21.5) |
| 1.4 | C$_5$H$_{11}$ | C | D | — | 55.0 | (−20.5) |
| 1.4 | C$_4$H$_9$O | C | D | — | 68.5 | (60) |
| 1.5 | C$_5$H$_{11}$ | B | Known | — | 74.5 | [−18.0]$^{(i)}$ |
| 1.5 | C$_4$H$_9$O | B | Known | — | 101.0 | [25.0]$^{(iii)}$ |
| 1.6 | C$_5$H$_{11}$ | B | Known | — | 32.0 | [−45.0]$^{(ii)}$ |
| 1.6 | C$_4$H$_9$O | B | Known | — | 56.0 | (−1.5) |
| 1.7 | C$_5$H$_{11}$ | B | D | — | 36.5 | (−67) |
| 1.7 | C$_4$H$_9$O | B | D | — | 63.0 | (−31.5) |

( ) represents monotropic transitions.

TABLE 5

| Structure | R | Acid Route | Phenol Route | K-N(°C.) | K-I(°C.) | N-I(°C.) |
|---|---|---|---|---|---|---|
| 1.8 | C$_5$H$_{11}$ | Known | A | 96.5 | — | 150.5 |
| 1.8 | C$_4$H$_9$O | Known | A | 114.5 | — | 195.0 |
| 1.9 | C$_5$H$_{11}$ | C | Known | 103.0 | — | 225.0 |
| 1.9 | C$_4$H$_9$O | C | Known | 94.0 | — | 259.5 |
| 1.10 | C$_5$H$_{11}$ | C | A | 112.5 | — | 187.5 |
| 1.10 | C$_4$H$_9$O | C | A | 115.0 | — | 219.5 |
| 1.11 | C$_5$H$_{11}$ | C | A | 98.0 | — | 143.5 |
| 1.11 | C$_4$H$_9$O | C | A | 104.0 | — | 184.0 |
| 1.12 | C$_5$H$_{11}$ | B | Known | 109.5 | — | 191.0 |
| 1.12 | C$_4$H$_9$O | B | Known | 94.0 | — | 223.0 |

TABLE 5-continued

| Structure | R | Acid Route | Phenol Route | K-N(°C.) | K-I(°C.) | N-I(°C.) |
|---|---|---|---|---|---|---|
| 1.13 | $C_5H_{11}$ | B | A | 116.5 | — | 158.0 |
| 1.13 | $C_4H_9O$ | B | A | 103.0 | — | 194.0 |
| 1.14 | $C_5H_{11}$ | B | A | 89.0 | — | 121.0 |
| 1.14 | $C_4H_9$ | B | A | 102.0 | — | 161.5 |

In Table 4, (i), (ii), (iii) indicate that the transitions observed were virtual, and were observed in 14, 13 and 21 wt. % mixtures of the compounds in the known nematic liquid crystal mixture E7 which has a composition:

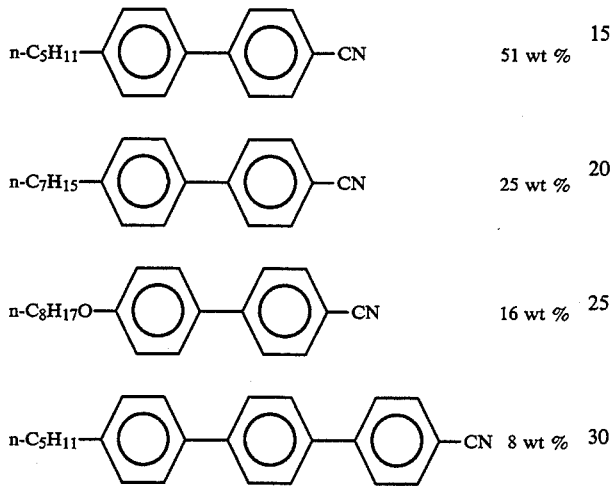

In table 6 below properties of various compounds of formula I having the structures indicated (see table 1) are listed. The values of viscosity ($\eta$ cps), $\epsilon\perp$ and $\Delta\epsilon$ are extrapolated from a 10 weight % solution of the compound in a 1:1:1 by weight mixture of compounds of formula 3.8 (see table 3) having the $R^3:R^4$ combinations n-$C_3H_7$:$C_2H_5$, n-$C_3H_7$:n-$C_5H_{11}$, n-$C_5H_{11}$:$C_2H_5$. These solutions are examples of liquid crystal mixtures of the invention.

TABLE 6

| Structure | R | $\eta$ | Dipole | $\epsilon\perp$ | $\Delta\epsilon$ |
|---|---|---|---|---|---|
| 1.1 | n-$C_5H_{11}$ | | 7.2 | 9.7 | 61 |
| 1.2 | " | | 6.4 | 8.6 | 39 |
| 1.3 | " | | 7.1 | 10.4 | 50.6 |
| 1.4 | " | | 7.7 | 10.0 | 64.9 |
| 1.5 | " | | 6.8 | 7.9 | 36.3 |
| 1.6 | " | 86 | 7.4 | 19.0 | 40.0 |
| 1.7 | " | | 8.0 | 11.9 | 59.3 |
| 1.9 | " | 420 | 7.5 | 10.0 | 54 |
| 1.1 | n-$C_4H_9O$ | | 7.8 | 10.2 | 66.8 |
| 1.2 | " | | 6.9 | 7.5 | 42.6 |
| 1.3 | " | | 7.5 | 10.7 | 43.8 |
| 1.4 | " | | 8.0 | 11.3 | 69.5 |
| 1.5 | " | | | 7.6 | 44.5 |
| 1.6 | " | | 7.9 | 9.9 | 54.2 |
| 1.7 | " | | 8.3 | 10.7 | 58.5 |

Figure 7:
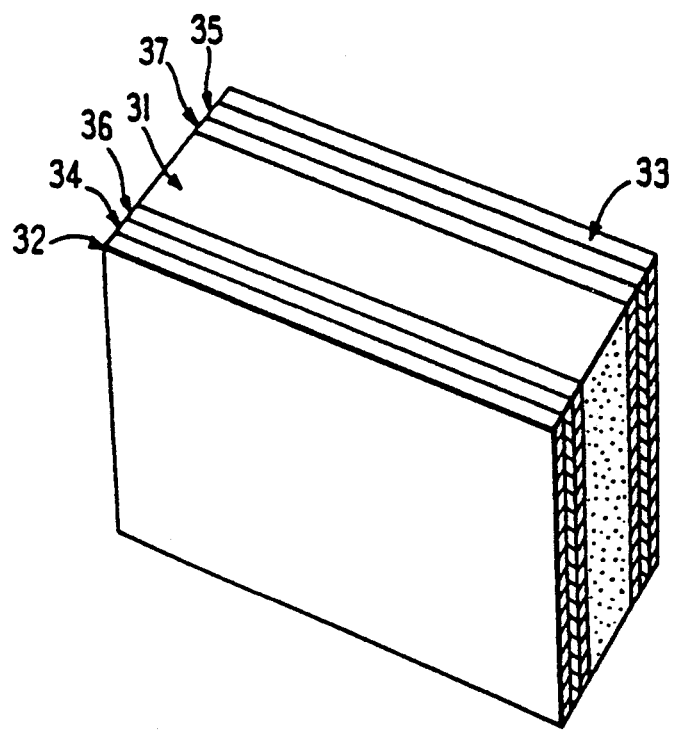
FIG. 7 showing a liquid crystal electro-optic display device.

Referring to FIG. 7, a liquid crystal electro optical display device comprises a layer of a liquid crystal material 31 between a front glass support plate 32 and a back glass support plate 33. The front glass plate 32 is coated on the inner surface thereof with a transparent conducting layer 34 eg tin oxide, to form an electrode. The back glass plate 33 is also coated on the inside surface thereof with a conductive layer 35. If light is to be transmitted through the device the back electrode 15 and the back plate 33 are also transparent and made of the same materials as the front plate and electrode 32 and 34. If the device is to reflect light the back electrode 35 may be made reflective, eg of aluminium. The front and back electrodes 34, 35 are coated with a transparent aligning layer 36, 37 eg of poly-vinyl alcohol which have each been rubbed prior to assembly of the device in a single rubbing direction. On assembly the rubbing directions of the layers 36, 37 are arranged orthogonal to each other. In operation the electrodes 34, 35 are connected to a source of voltage (not shown).

A suitable liquid crystal material 32 is a 14, 13, or 21 weight % mixture of one of the compounds:

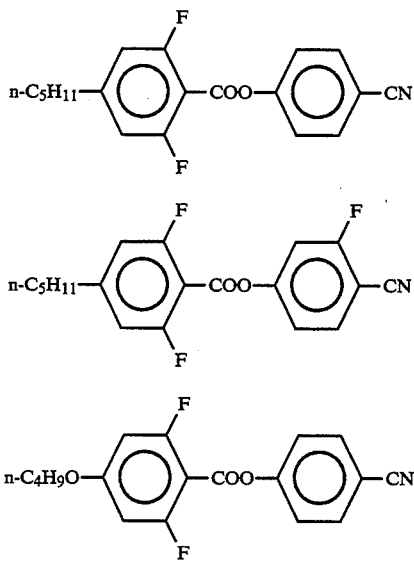

in the material E7 referred to above.

We claim:

1. A compound having the formula I:

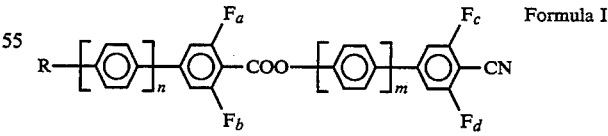

in which R is $R^1$ or $R^1O$ wherein $R^1$ is $C_{1\text{-}12}$ alkyl, m and n are 0 or 1 provided that (n+m) is 1, each of a, b, c and d are independently 0 or 1, provided (a+b+c+d) is not zero and excluding the cases where a and b are 0 and one of c and d is 0, where n, c and d are 0, m is 1 and (a+b)=1, where n is 0, m is 1, (a+b)=1 and (c+d)=1, and where n is 0, m is 1, (a+b)=0 and (c+d)=2.

2. A compound according to claim 1 having the formula:

3. A compound according to claim 1 having the formula:

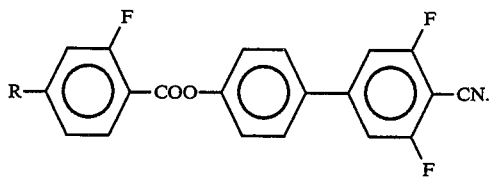

4. A compound according to claim 1 having the formula:

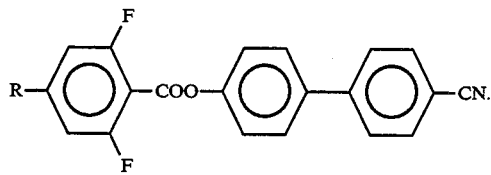

5. A compound according to claim 1 having the formula:

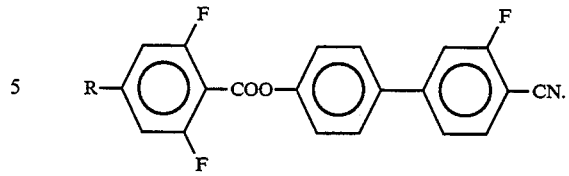

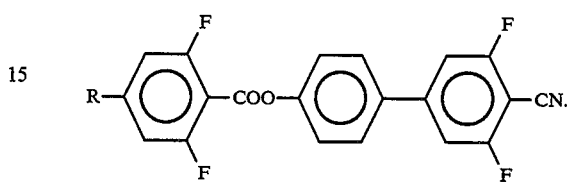

6. A compound according to claim 1 wherein R contains from 3 to 8 carbon atoms inclusive.

7. A compound according to claim 6 wherein $R^1$ is n-alkyl or an asymmetrically substituted alkyl group.

8. A compound according to claim 1 wherein R is n-alkyl or n-alkoxy.

9. A liquid crystal material being a mixture of compounds where at least one is a compound of claim 1.

10. A nematic liquid crystal display device containing a liquid crystal material as claimed in claim 9.

* * * * *